United States Patent
Wu et al.

(10) Patent No.: US 11,071,556 B2
(45) Date of Patent: Jul. 27, 2021

(54) POSITIONING GUIDING DEVICE AND POSITIONING METHOD THEREOF FOR ACETABULUM REAMING AND ACETABULAR CUP PROSTHESIS IMPLANTATION

(71) Applicant: The first Affiliated hospital of Sun Yat-sen University, Guangzhou (CN)

(72) Inventors: Peihui Wu, Guangzhou (CN); Weiming Liao, Guangzhou (CN); Ming Fu, Guangzhou (CN); Puyi Sheng, Guangzhou (CN)

(73) Assignee: The first Affiliated hospital of Sun Yat-sen University, Guangzhou (CN)

( * ) Notice: Subject to any disclaimer, the term of this patent is extended or adjusted under 35 U.S.C. 154(b) by 387 days.

(21) Appl. No.: 15/577,349

(22) PCT Filed: Dec. 28, 2016

(86) PCT No.: PCT/CN2016/112723
§ 371 (c)(1),
(2) Date: Nov. 1, 2018

(87) PCT Pub. No.: WO2018/076530
PCT Pub. Date: May 3, 2018

(65) Prior Publication Data
US 2019/0380720 A1 Dec. 19, 2019

(30) Foreign Application Priority Data
Oct. 27, 2016 (CN) .......................... 201610957842.5

(51) Int. Cl.
*A61B 17/17* (2006.01)
*A61B 34/10* (2016.01)
(Continued)

(52) U.S. Cl.
CPC ...... *A61B 17/1746* (2013.01); *A61B 17/1615* (2013.01); *A61B 34/10* (2016.02);
(Continued)

(58) Field of Classification Search
CPC . A61B 17/1742; A61B 17/1746; A61B 90/11; A61B 17/1615; A61B 34/10; A61F 2/4609
See application file for complete search history.

(56) References Cited

U.S. PATENT DOCUMENTS

| 8,992,538 B2 * | 3/2015 | Keefer ............... A61B 17/1746 606/87 |
| 2007/0106305 A1 * | 5/2007 | Kao ....................... A61B 90/11 606/130 |

(Continued)

FOREIGN PATENT DOCUMENTS

| CN | 101711695 A | 5/2010 |
| CN | 102283689 A | 12/2011 |

(Continued)

*Primary Examiner* — Si Ming Ku
(74) *Attorney, Agent, or Firm* — Bayramoglu Law Offices LLC (57) ABSTRACT

The present invention has a simple structure which is convenient in preparation and easy to use. Moreover, in combination with three-dimensional preoperative analysis and rapid molding technology, the present invention has a high customized precision and clinical applicability, and is cost-effective. Based on the three-dimensional preoperative analysis and 3d printing model, the problems of high technical difficulty and cost of the customized accurate implantation of acetabular cup prosthesis in the total hip arthroplasty can be effectively solved, so that the learning curve of operator can be shortened. The present invention can realize the customized accurate implantation of acetabular cup prosthesis without fitting the positioning guiding module with the articular surface area, so that the assisted position- (Continued)

ing and assisted reaming depth determination are realized without removing the guiding module when the acetabulum is being reamed, thus the accuracy of the assisted positioning can be guaranteed.

7 Claims, 6 Drawing Sheets

(51) Int. Cl.
*A61B 17/16* (2006.01)
*A61F 2/46* (2006.01)
*A61B 17/00* (2006.01)

(52) U.S. Cl.
CPC .. *A61F 2/4609* (2013.01); *A61B 2017/00398* (2013.01); *A61B 2017/00477* (2013.01); *A61B 2034/104* (2016.02); *A61B 2034/105* (2016.02); *A61B 2034/108* (2016.02); *A61F 2002/4627* (2013.01); *A61F 2002/4633* (2013.01); *A61F 2002/4687* (2013.01)

(56) References Cited

U.S. PATENT DOCUMENTS

2014/0358151 A1* 12/2014 Murphy ................ A61F 2/4657
606/91
2015/0190151 A1 7/2015 Budhabhatti et al.

FOREIGN PATENT DOCUMENTS

| CN | 102740790 A | 10/2012 |
|---|---|---|
| CN | 103153240 A | 6/2013 |
| CN | 103169553 A | 6/2013 |
| CN | 204106119 U | 1/2015 |

* cited by examiner

POSITIONING GUIDING DEVICE AND POSITIONING METHOD THEREOF FOR ACETABULUM REAMING AND ACETABULAR CUP PROSTHESIS IMPLANTATION

CROSS REFERENCE TO RELATED APPLICATIONS

This application is the national phase entry of International Application No. PCT/CN2016/112723, filed on Dec. 28, 2016, which is based upon and claims priority to Chinese Patent Application No. CN2016109578425 filed on Oct. 27, 2016, the entire contents of which are incorporated herein by reference.

TECHNICAL FIELD

The present invention relates to the field of medical instrument technology, and more particularly to a positioning guiding device and positioning method thereof for acetabulum reaming and acetabular cup prosthesis implantation in a total hip arthroplasty.

BACKGROUND

One of the essential goals for artificial total hip arthroplasty is to obtain a stable hip joint and a stable joint prosthesis. During the operation, the implantation position of the acetabular cup prosthesis should be able to recover the center of the normal rotation of the hip joint as much as possible and keep the abduction angle and anteversion angle within a safe range, while an adequate host bone-acetabular cup coverage is obtained, so that a better long-term survival rate of prosthesis, and a reduction of complications such as postoperative prosthesis loosening, prosthetic impingement, joint dislocation etc., can be obtained.

Currently, the most commonly used clinical positioning method for acetabulum filing and acetabular cup implantation in artificial total hip arthroplasty is that the angle direction and filing depth for the installation position of the prosthesis is subjectively determined by the operator based on the angle of the acetabulum filing direction and the acetabular cup inserting direction with respect to the direction of ground and the direction of the coronal plane where the patient's body is located, with reference to the original anatomical structure of the acetabulum. In the operation, many factors such as the operative position of patient, the pelvis position, the lesion and anatomical variation of the pelvis and acetabulum structure etc., will affect the direction of the acetabulum reaming and acetabular cup implantation and cause a position deviation therefor, so that the operator cannot ream the acetabulum and implant the acetabular cup prosthesis in accordance with the desired angle and position based on the subjective determination. Due to the potential errors, the traditional positioning technology of acetabular cup has a high risk, especially for patients who suffer from severe deformities and lesions in the acetabular structure, which is also confirmed by clinical studies. Therefore, the potential risk of the occurrence of errors is high if the conventional acetabulum reaming device and positioning method are used, which easily leads to a position deviation of postoperative acetabular cup prosthesis implantation, and thus affecting the surgical outcomes.

The computer assisted navigation and positioning technology and 3D printed customized guide positioning technology are two new technologies for assisting the reaming and positioning of acetabulum.

The computer assisted navigation and positioning technology is a positioning technology, in which the data of acetabulum profile and the installation angle and reaming depth of acetabular cup prosthesis etc. are quantified to determine whether there are information errors based on the specific situation during the operation, and correction of the information errors is timely performed. The computer assisted navigation and positioning technology can greatly improve the positioning accuracy of acetabular cup prosthesis in the hip arthroplasty. However, since the computer assisted navigation and positioning technology has a high requirement for the apparatus, and is time-consuming in the operation, and thus the computer assisted navigation and positioning technology cannot be widely used. For the 3D printed customized ostectomy guide positioning technology, the installation position and angle of the acetabular cup are determined based on the rebuilt preoperative pelvic CT or MR images by means of the computer assisted design. The 3D printing technology is used to build customized positioning guiding module for patients. During the operation, the reaming direction is determined by fitting and matching the 3d printed customized positioning guiding module with the specific area of the articular surface. However, since the positioning guiding module needs to fit with the area of articular surface, the guiding module should be removed when the acetabulum is reamed, so as to ream the bone of the articular surface. Therefore, the real-time assisted positioning and assisted reaming depth determination are hard to be realized, so that the accuracy of the assisted positioning cannot be ensured.

In view of the above issues, it is a major issue to provide a cost-effective positioning guiding device and a positioning method thereof for customized acetabulum reaming and acetabular cup implantation. The positioning guiding device and the positioning method have a higher customized accuracy and clinical applicability, and thus can improve the accuracy of the acetabular cup prosthesis implantation and the postoperative effect.

SUMMARY OF THE INVENTION

Regarding the drawbacks of the prior art, the present invention provides a positioning guiding device and positioning method thereof for acetabulum reaming and acetabular cup prosthesis implantation in the total hip arthroplasty.

The objective of the present invention is realized by the following technical solutions.

A positioning guiding device for acetabulum reaming and acetabular cup prosthesis implantation includes: a sleeve handle and a plurality of slide arms slidably arranged on the sleeve handle, each slide arm is connected to a positioning assembly, the positioning assembly is rotatably adjustable with respect to the slide arm to be fastened and fixed, and the sleeve handle is provided with a hollow inner cavity.

Furthermore, the positioning assembly includes a clamping joint and a support head, an end of the clamping joint is rotatably connected to the slide arm to form a first movable joint, and an other end of the clamping joint is rotatably connected to the support head to form a second movable joint, the clamping joint is provided with a joint locking nut to lock the first movable joint and the second movable joint.

Furthermore, both ends of the clamping joint are respectively provided with a first joint fossa and a second joint fossa, a tail end of the slide arm is provided with a first rotary ball head which is matched with the first joint fossa, an end of the support head is provided a second rotary ball head which is matched with the second joint fossa.

Furthermore, the joint locking nut is rotatably arranged on the clamping joint. When the joint locking nut is unlocked, both the first movable joint and the second movable joint rotate freely, and when the joint locking nut is locked, both the first movable joint and the second movable joint are fixed and cannot move.

Furthermore, an other end of the support head is provided with a positioning groove to abut against an edge of an outer opening of the acetabulum.

Furthermore, the sleeve handle is provided with a plurality of slide grooves, an upper end of the slide arm is provided with a slide portion which is matched with the slide grooves, and a locking bolt to tightly fasten and fix the slide portion in the slide groove is further provided.

Preferably, the sleeve handle is composed of a main body arm and a main rod locking block, and the main body arm and the main rod locking block are matched with each other to form a sleeve and are connected to each other through an open-close connection assembly.

Furthermore, a moving distance of the slide portion in the slide groove is 60 mm.

Furthermore, the clamping joint is composed of a first clamping block and a second clamping block, the first clamping block and the second clamping block are matched with each other, and a middle portion of the first clamping block and the second clamping block is each provided with a mounting hole to mount the joint locking nut.

A positioning method of a positioning guiding device used for acetabulum reaming and acetabular cup prosthesis implantation in a total hip arthroplasty includes the following steps.

S1, determining an optimal position of a customized acetabular cup prosthesis implantation, wherein, based on scanned pelvic CT or MRI data, using a three-dimensional modeling image analysis software, with reference to a bone mass distribution and the lesion characteristics of the acetabulum of the patient, a preferred size, implantation angle and position of the acetabular cup prosthesis are measured and analyzed; by doing so, not only an ideal contained area of the autogenous bone can be obtained, but also the acetabular cup prosthesis is located within a safe angle range and at a safe position of the acetabular cup; also, not only a good initial stability of the acetabular cup prosthesis is guaranteed, but also the risk of a prosthetic impingement is reduced as much as possible, so as to improve the stability of joint;

S2, rapidly molding three-dimensional models of an acetabular cup implantation solution designed before an operation at a ratio of 1:1; wherein, there are two models, the first model is an acetabulum model implanted with an acetabular cup prosthesis having a direction indicating rod according to an optimized operation scheme; the second model is an acetabulum model which is reamed according to the optimized operation scheme, namely, a part of bone of the acetabulum model is reamed off;

S3, determining a position of each slide arm and a rotation angle of each movable joint in a positioning assembly; wherein, a sleeve of the positioning guiding device used for acetabulum reaming and acetabular cup implantation is sleeved outside the direction indicating rod of the acetabular cup prosthesis of the first model molded by a rapid molding, and an end of the sleeve connected to the slide arm is positioned toward the acetabulum model; the locking bolt of each slide arm and each movable joint of the positioning assembly are unlocked, and a position of a tip of each support head is adjusted according to an exposure range of the acetabulum in the operation, so that an exposed space can be sufficiently used by the support head, and the support head can contact with an edge of an outer opening of the acetabulum in the model; subsequently, each movable joint is fastened and fixed to ensure a stable positioning after a positioning tip of the support head contacts with the edge of the outer opening of the acetabulum; by doing so, the position at the edge of the outer opening of the acetabulum determined by four support heads corresponds to a direction of the direction indicating rod of the acetabular cup prosthesis;

S4, determining a reaming depth of the acetabulum; wherein, after the positioning guiding device used for acetabulum reaming and acetabular cup implantation is removed from the first model, an acetabulum reaming rod is inserted, and the acetabulum reaming rod is preferably selected from one of acetabulum reamers with different sizes; firstly, the tip of each of the four support heads is matched with the edge of the outer opening of the acetabulum of the second model, and the tips of the four support heads simultaneously contact the edge of the outer opening of the acetabulum to make sure that a direction of the acetabulum reamer is the same as a direction of the direction indicating rod of the acetabular cup prosthesis in the first model; subsequently, the acetabulum reamer is pushed along a reaming direction to make the acetabulum reamer contact a bottom portion of an acetabulum fossa of the second model, and the position is the desired position to ream by the acetabulum reamer; after that, a position of a position locking ring is set at the acetabulum reaming rod located at an other end of the sleeve of the positioning guiding device used for acetabulum reaming and acetabular cup implantation to make the position locking ring just contact an upper end port of the sleeve handle or have a certain distance to the upper end opening of the sleeve handle for a deeper reaming; by doing so, when the acetabulum reamer reams to the desired depth, the position locking ring at the reaming rod would contact with the end port of the sleeve to prevent a deeper reaming;

S5, performing a practical acetabulum reaming and acetabular cup implantation; wherein according to an operating approach of a conventional total hip arthroplasty, a bone edge of the opening of the acetabulum is adequately exposed; the adjusted tips of the four support heads of the positioning guiding device used for acetabulum reaming and acetabular cup implantation are matched with the bone edge of the opening of the acetabulum to make the tips of the four support heads synchronously contact with the bone edge of the opening of the acetabulum to make sure that the direction of the acetabulum reamer is the same as the direction of the direction indicating rod of the acetabular cup prosthesis of the first model; after that, the acetabulum reamer with a proper size is selected, and the acetabulum reamer is pushed along the reaming direction to ream until the position locking ring at the reaming rod contacts the end port of the sleeve handle, and the reaming is finished.

Compared with the prior art, the present invention has the following advantages.

1. The present invention has a simple structure which is convenient in preparation and easy to use. Moreover, in combination with three-dimensional preoperative analysis and rapid molding technology, the present invention has a high customized precision and clinical applicability, and is cost-effective.

2. Based on the three-dimensional preoperative analysis and 3d printing model, the problems of high technical difficulty and cost of the customized accurate implantation of acetabular cup prosthesis in the total hip arthroplasty can be effectively solved, so that the learning curve of operator can be shortened.

3. The present invention can realize the customized accurate implantation of acetabular cup prosthesis without fitting the positioning guiding module with the articular surface area, so that the assisted positioning and assisted reaming depth determination are realized without removing the guiding module when the acetabulum is being reamed, thus the accuracy of the assisted positioning can be guaranteed.

The designator references in the figures are described as follows. 1. sleeve handle, 11. main body arm, 12. main rod locking block, 2. slide arm, 21. first rotary ball head, 22. slide portion, 23. locking bolt, 3. hollow inner cavity; 4. clamping joint, 41. first clamping block, 42. second clamping block, 43. mounting hole, 44. first joint fossa, 45. second joint fossa, 5. support head, 51. second rotary ball head, 52. positioning groove, 6. joint locking nut, 7. slide groove, 8. open-close connection assembly.

DETAILED DESCRIPTION OF THE INVENTION

The present invention will be described in detail with reference to the drawings and specific embodiments hereinafter.

Embodiment 1

Figure 1:
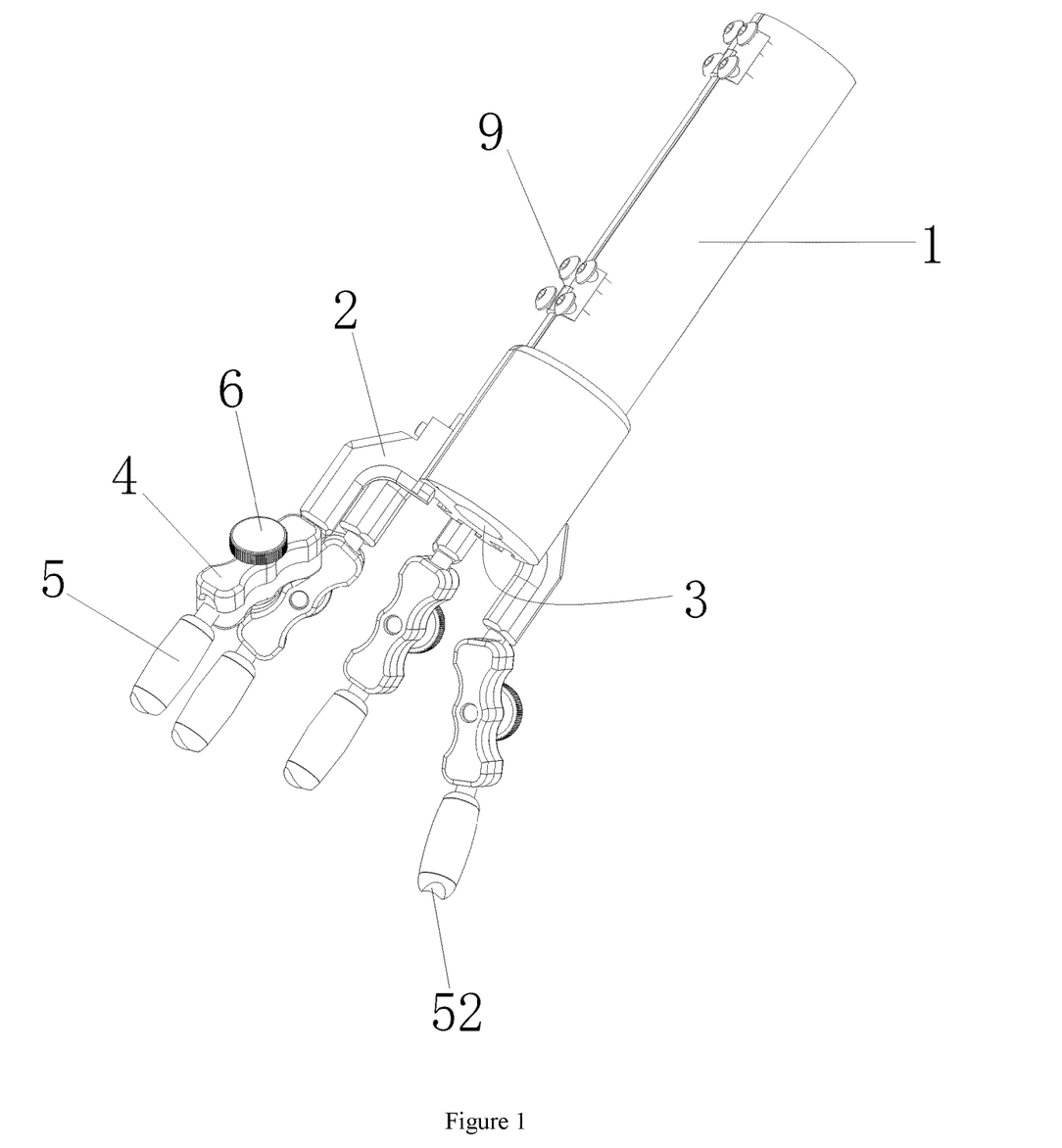
FIG. 1 is a structural schematic diagram of a positioning guiding device for acetabulum reaming and acetabular cup prosthesis implantation of the present invention.
Figure 2:
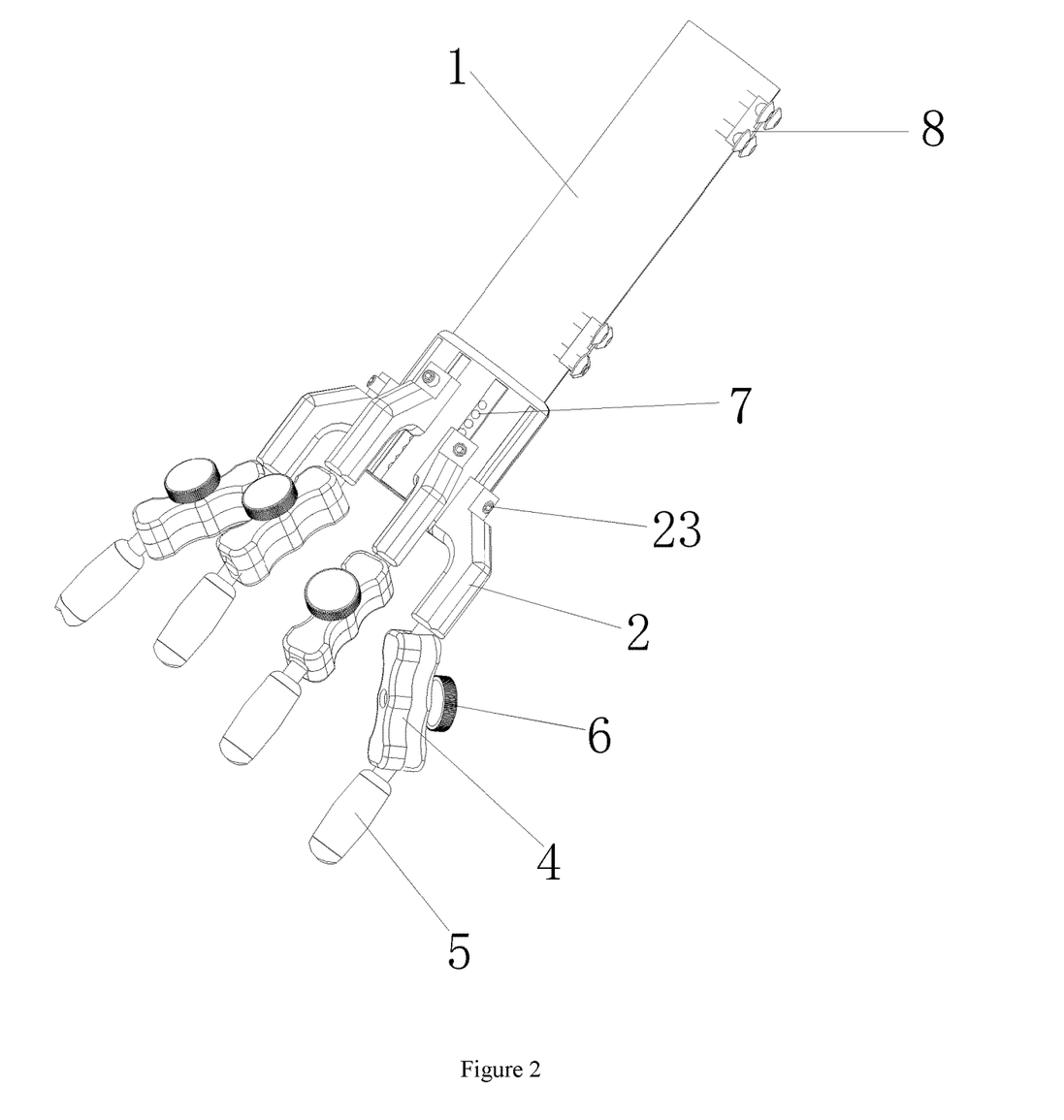
FIG. 2 is a structural schematic diagram showing another view of the positioning guiding device for acetabulum reaming and acetabular cup prosthesis implantation of the present invention.

As shown in FIG. 1, a positioning guiding device for acetabulum reaming and acetabular cup prosthesis implantation is provided by the present embodiment. The positioning guiding device includes a sleeve handle 1 and a plurality of slide arms 2 slidably arranged on the sleeve handle 1. Each slide arm 2 is connected to a positioning assembly. Each positioning assembly is rotatably adjustable with respect to the slide arm 2 and is locked and fixed. The sleeve handle 1 is provided with a hollow inner cavity 3.

The present invention has a simple structure which is convenient in preparation and easy to use. Moreover, in combination with three-dimensional preoperative analysis and rapid molding technology, the present invention has a high customized precision and clinical applicability, and is cost-effective. Based on the three-dimensional preoperative analysis and 3d printing model, the problems of high technical difficulty and cost of the customized accurate implantation of acetabular cup prosthesis in the total hip arthroplasty can be effectively solved, so that the learning curve of operator can be shortened. The present invention can realize the customized accurate implantation of acetabular cup prosthesis without fitting the positioning guiding module with the articular surface area, so that the assisted positioning and assisted reaming depth determination are realized without removing the guiding module when the acetabulum is being reamed, thus the accuracy of the assisted positioning can be guaranteed.

Furthermore, the positioning assembly includes a clamping joint 4 and a support head 5. An end of the clamping joint 4 is rotatably connected to the slide arm 2 to form a first movable joint, and the other end of the clamping joint 4 is rotatably connected to the support head 5 to form a second movable joint. The clamping joint 4 is provided with a joint locking nut 6 to lock the first movable joint and the second movable joint.

The first movable joint and the second movable joint are independent movable mechanisms. An angle and direction between the movable mechanisms and the slide arm 2 can be flexibly adjusted. By doing so, not only an ideal contained area of the autogenous bone can be obtained, but also the acetabular cup prosthesis is located within a safe angle range and at a safe position of the acetabular cup. Also, not only a good initial stability of the acetabular cup prosthesis is guaranteed, but also the risk of a prosthetic impingement is reduced as much as possible, so as to improve the stability during use.

Figure 4:
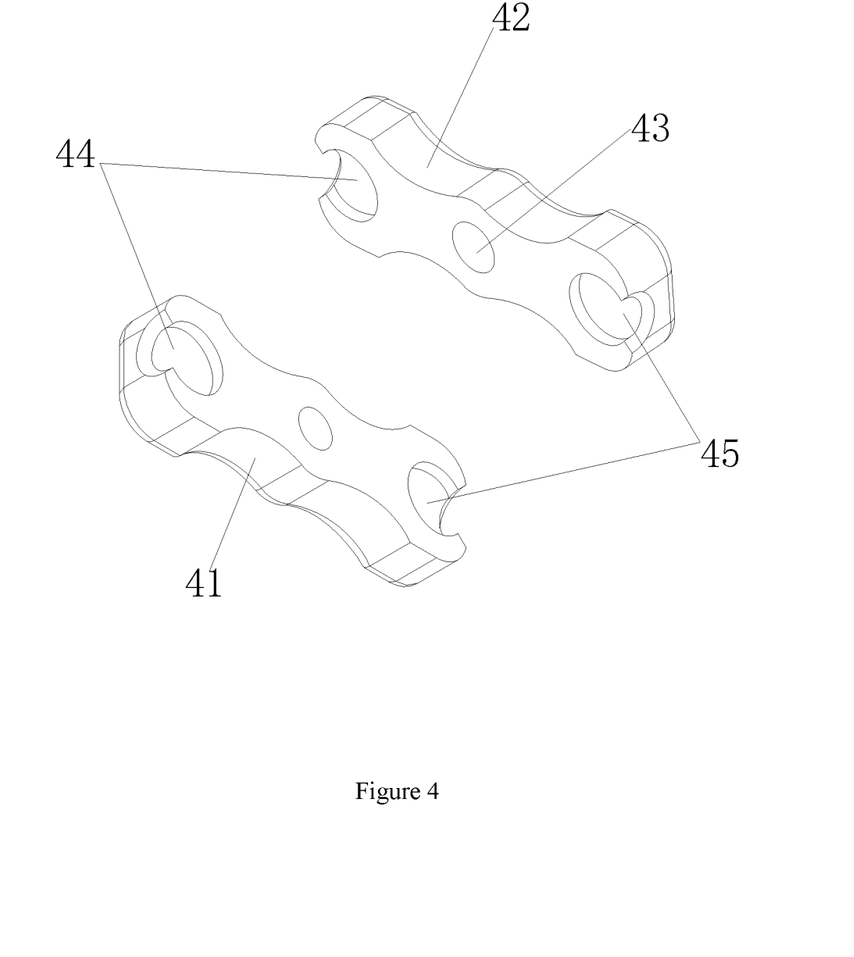
FIG. 4 is a structural schematic diagram of the clamping joint of the present invention.
Figure 5:
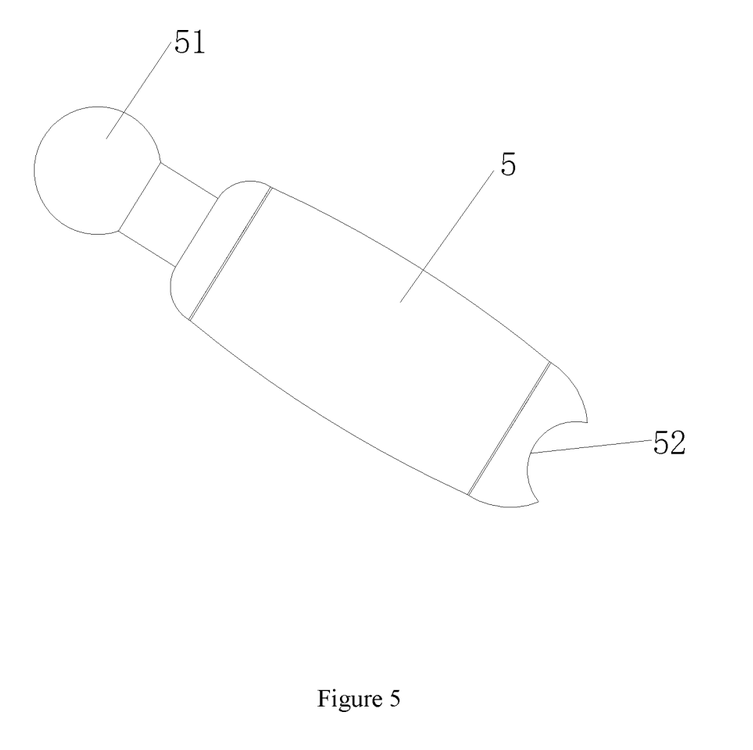
FIG. 5 is a structural schematic diagram of the support head of the present invention.
Figure 6:
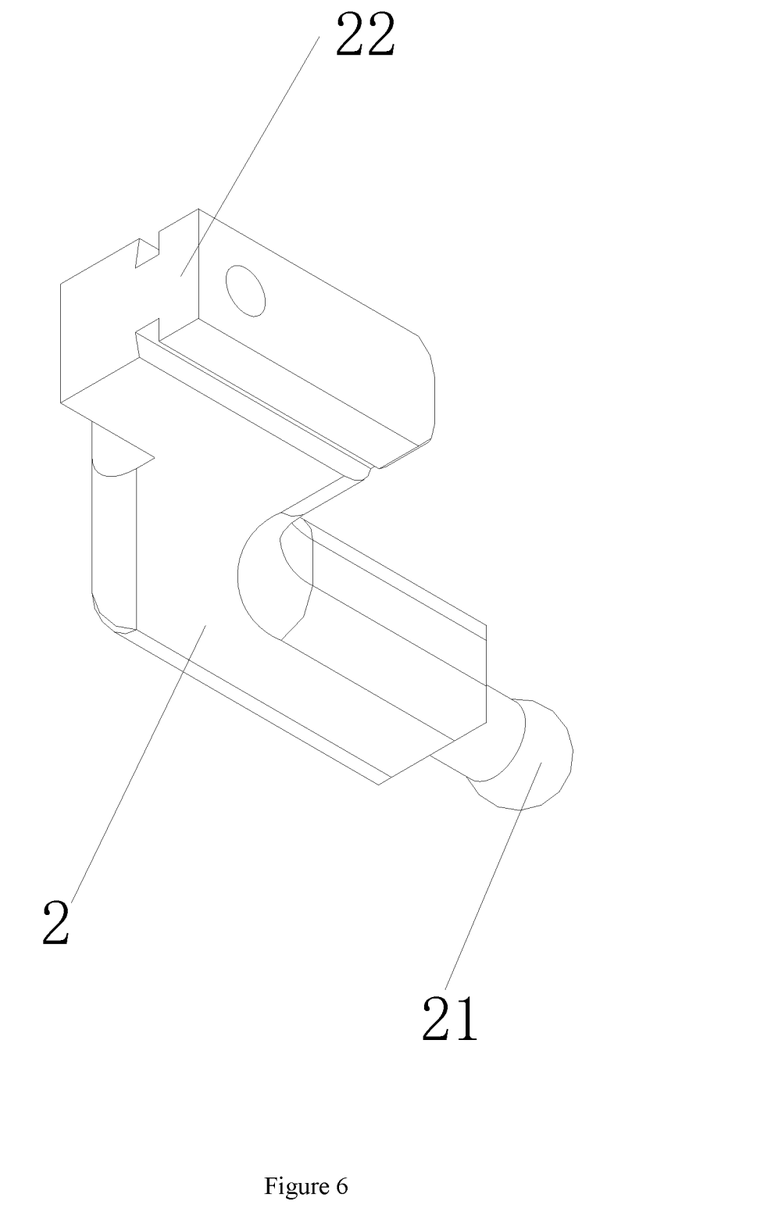
FIG. 6 is a structural schematic diagram of the slide arm of the present invention.

Furthermore, both ends of the clamping joint 4 are respectively provided with a first joint fossa 44 and a second joint fossa 45. A tail end of the slide arm 2 is provided with a first rotary ball head 21 which is matched with the first joint fossa 44, an end of the support head 5 is provided a second rotary ball head 51 which is matched with the second joint fossa 45. The joint locking nut 6 is rotatably arranged on the clamping joint 4, and the clamping joint 4 is flexibly rotatable to adjust the direction and is easily fastened and fixed by the joint locking nut 6. When the joint locking nut is unlocked, the first rotary ball head 21 freely rotates inside the first joint fossa 44 and the second rotary ball head 51 freely rotates inside the second joint fossa 45, namely, both the first movable joint and the second movable joint rotate freely. When the joint locking nut is locked, the first rotary ball head 21 is fixedly locked inside the first joint fossa 44, and the second rotary ball head 51 is fixedly locked inside the second joint fossa 45, both the first movable joint and the second movable joint are fixed and cannot move.

Furthermore, the other end of the support head 5 is provided with a positioning groove 52 to abut against an edge of an outer opening of the acetabulum. By using the positioning groove 52, the stability of abutting against the edge of the outer opening of the acetabulum is greatly improved, so as to prevent the slippage due to the shaking, and thus the stability during use is improved.

Figure 3:
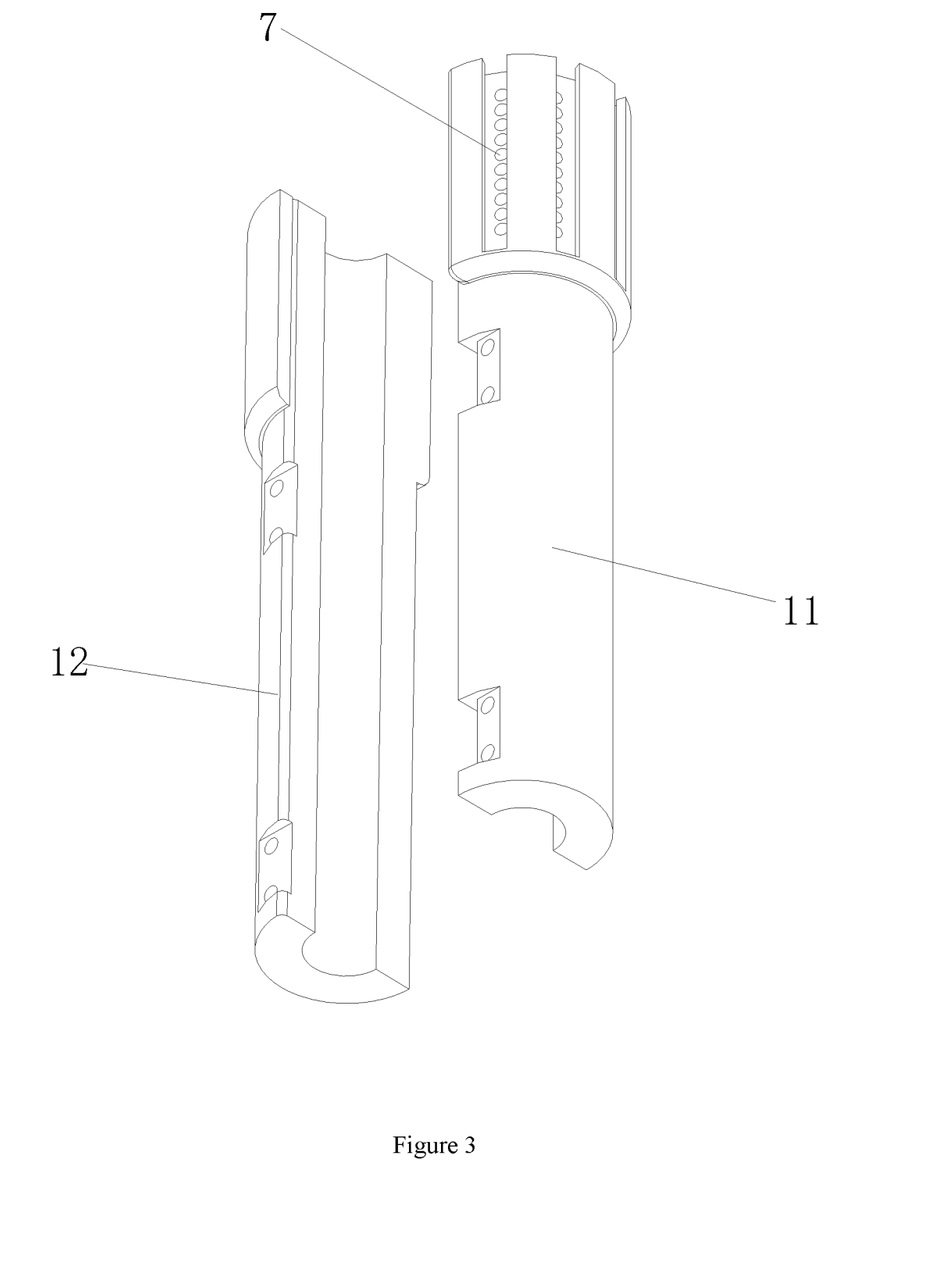
FIG. 3 is a structural schematic diagram of the sleeve handle of the present invention.

Furthermore, the sleeve handle 1 is provided with a plurality of slide grooves 7, and an upper end of the slide arm 2 is provided with a slide portion 22 which is matched with the slide grooves 7. The slide portion 22 can slide up and down along the slide groove 7 by a certain distance to adjust the position of the positioning assembly on the slide arm 2. Preferably, the moving distance of the slide arm 2 is 60 mm. A locking bolt 23 is further provided to lock and fix the slide portion 22 in the slide groove 7. When the slide portion 22 is adjusted to a desired position, the slide portion 22 is fastened and fixed through the locking bolt 23.

Preferably, the sleeve handle 1 is composed of a main body arm 11 and a main rod locking block 12, and the main body arm and the main rod locking block are matched with each other to form a sleeve and are connected to each other through an open-close connection assembly 8. The sleeve handle 1 can be opened to insert the direction indicating rod and the acetabulum reaming rod, and thus the structure is practical.

Furthermore, the clamping joint 4 is composed of a first clamping block 41 and a second clamping block 42, and the first clamping block and the second clamping block are matched with each other. A middle portion of the first clamping block and the second clamping block is each provided with a mounting hole 43 to mount the joint locking nut 6. The first clamping block 41 and the second clamping block 42 can be easily adjusted via the joint locking nut 6, so as to achieve the purpose of unlocking or locking each movable joint.

Embodiment 2

A positioning method of a positioning guiding device used for acetabulum reaming and acetabular cup prosthesis implantation in a total hip arthroplasty is provided by the present embodiment, which includes the following steps.

S1, determining an optimal position of a customized acetabular cup prosthesis implantation, wherein, based on scanned pelvic CT or MRI data, using a three-dimensional modeling image analysis software, with reference to a bone mass distribution and the lesion characteristics of the acetabulum of the patient, a preferred size, implantation angle and position of the acetabular cup prosthesis are measured and analyzed; by doing so, not only an ideal contained area of the autogenous bone can be obtained, but also the acetabular cup prosthesis is located within a safe angle range and at a safe position of the acetabular cup; also, not only a good initial stability of the acetabular cup prosthesis is guaranteed, but also the risk of a prosthetic impingement is reduced as much as possible, so as to improve the stability of joints;

S2, rapidly molding three-dimensional models of an acetabular cup implantation solution designed before an operation at a ratio of 1:1; wherein, there are two models, the first model is an acetabulum model implanted with an acetabular cup prosthesis having a direction indicating rod according to an optimized operation scheme; the second model is an acetabulum model which is reamed according to the optimized operation scheme, namely, a part of bone of the acetabulum model is reamed off;

S3, determining a position of each slide arm 2 and a rotation angle of each movable joint in a positioning assembly; wherein, a sleeve of the positioning guiding device used for acetabulum reaming and acetabular cup implantation is sleeved outside the direction indicating rod of the acetabular cup prosthesis of the first model molded by a rapid molding, and an end of the sleeve connected to the slide arm is positioned toward the acetabulum model; the locking bolt 23 of each slide arm 2 and each movable joint of the positioning assembly are unlocked, and a position of a tip of each support head is adjusted according to an exposure range of the acetabulum in the operation, so that an exposed space can be sufficiently used by the support head, and the support head can contact with an edge of an outer opening of the acetabulum in the model; subsequently, each movable joint is fastened and fixed to ensure a stable positioning after a positioning tip of the support head 5 contacts with the edge of the outer opening of the acetabulum; by doing so, the position at the edge of the outer opening of the acetabulum determined by four support heads corresponds to a direction of the direction indicating rod of the acetabular cup prosthesis;

S4, determining a reaming depth of the acetabulum; wherein, after the positioning guiding device used for acetabulum reaming and acetabular cup implantation is removed from the first model, an acetabulum reaming rod is inserted, and the acetabulum reaming rod is preferably selected from one of acetabulum reamers with different sizes; firstly, the tip of each of the four support heads 5 is matched with the edge of the outer opening of the acetabulum of the second model, and the tips of the four support heads 5 simultaneously contact the edge of the outer opening of the acetabulum to make sure that a direction of the acetabulum reamer is the same as a direction of the direction indicating rod of the acetabular cup prosthesis of the first model; subsequently, the acetabulum reamer is pushed along a reaming direction to make the acetabulum reamer contact a bottom portion of an acetabulum fossa of the second model, and the position is the desired position for the acetabulum reamer; after that, a position of a position locking ring is set at the acetabulum reaming rod located at an other end of the sleeve of the positioning guiding device used for acetabulum reaming and acetabular cup implantation to make the position locking ring just contact an upper end port of the sleeve handle 1 or have a certain distance to the upper end port of the sleeve handle 1 for a deeper reaming; by doing so, when the acetabulum reamer reams to the desired depth, the position locking ring at the reaming rod would contact with the end port of the sleeve to prevent a deeper reaming;

S5, performing a practical acetabulum reaming and acetabular cup implantation; wherein according to an operating approach of a conventional total hip arthroplasty, a bone edge of the opening of the acetabulum is adequately exposed; the adjusted tips of the four support heads 5 of the positioning guiding device used for acetabulum reaming and acetabular cup implantation are matched with the bone edge of the opening of the acetabulum to make the tips of the four support heads 5 synchronously contact with the bone edge of the opening of the acetabulum to make sure that the direction of the acetabulum reamer is the same as the direction of the direction indicating rod of the acetabular cup prosthesis of the first model; after that, the acetabulum reamer with a proper size is selected, and the acetabulum reamer is pushed along the reaming direction to ream until the position locking ring at the reaming rod contacts the end port of the sleeve handle 1, and the reaming is finished.

It should be understood by those of ordinary skill in the art that the embodiment described above is merely exemplary and is not intended to imply that the scope of the present invention including the claims is limited to these examples. Under the inventive concept of the present invention, the technical features in the above embodiment or in different embodiments can be combined. Moreover, there are many other variations in the various aspects of the present invention described above, which are not presented in detail for the sake of simplicity. Accordingly, any omissions, modifications, equivalent substitutions, or improvements etc. derived from the spirit and principles of the present invention, all fall within the scope of the present invention.

What is claimed is:

1. A positioning guiding device for acetabulum reaming and acetabular cup prosthesis implantation, comprising:
    a sleeve handle and a plurality of slide arms slidably arranged on the sleeve handle, each slide arm is connected to a positioning assembly, the positioning assembly is rotatably adjustable with respect to the slide arm to be fastened and fixed, and the sleeve handle is provided with a hollow inner cavity;

wherein the positioning assembly comprises a clamping joint and a support head, an end of the clamping joint is rotatably connected to the slide arm to form a first movable joint, and another end of the clamping joint is rotatably connected to the support head to form a second movable joint, wherein the clamping joint is provided with a joint locking nut to lock the first movable joint and the second movable joint, wherein both ends of the clamping joint are respectively provided with a first joint fossa and a second joint fossa, a tail end of the slide arm is provided with a first rotary ball head which is matched with the first joint fossa, an end of the support head is provided a second rotary ball head which is matched with the second joint fossa.

2. The positioning guiding device for acetabulum reaming and acetabular cup prosthesis implantation of claim 1, wherein the joint locking nut is rotatably arranged on the clamping joint, when the joint locking nut is unlocked, both the first movable joint and the second movable joint rotate freely, and when the joint locking nut is locked, both the first movable joint and the second movable joint are fixed.

3. The positioning guiding device for acetabulum reaming and acetabular cup prosthesis implantation of claim 1, wherein another end of the support head is provided with a positioning groove configured to abut against an edge of an outer opening of the acetabulum.

4. The positioning guiding device for acetabulum reaming and acetabular cup prosthesis implantation of claim 1, wherein the sleeve handle is provided with a plurality of slide grooves, an upper end of the slide arm is provided with a slide portion which is matched with the slide grooves, and the positioning guiding device further includes a locking bolt to tightly fasten and fix the slide portion in one of the plurality of slide grooves is further provided.

5. The positioning guiding device for acetabulum reaming and acetabular cup prosthesis implantation of claim 1, wherein the sleeve handle is composed of a main body arm and a main rod locking block, and the main body arm and the main rod locking block are matched with each other to form a sleeve and are connected to each other through an open-close connection assembly.

6. The positioning guiding device for acetabulum reaming and acetabular cup prosthesis implantation of claim 4, wherein a moving distance of the slide portion in the slide groove is 60 mm.

7. The positioning guiding device for acetabulum reaming and acetabular cup prosthesis implantation of claim 1, wherein the clamping joint is composed of a first clamping block and a second clamping block, the first clamping block and the second clamping block are matched with each other, and a middle portion of the first clamping block and the second clamping block is each provided with a mounting hole to mount the joint locking nut.

\* \* \* \* \*